United States Patent [19]

Plotkin et al.

[11] Patent Number: 5,045,572
[45] Date of Patent: Sep. 3, 1991

[54] RADIATION CURABLE CROSS LINKABLE COMPOSITIONS CONTAINING AN ALIPHATIC POLYFUNCTIONAL ALKENYL ETHER

[75] Inventors: Jeffrey S. Plotkin, Monsey, N.Y.; James A. Dougherty, Pequannock, N.J.; Fulvio J. Vara, Chester, N.J.; Paul D. Taylor, West Milford, N.J.

[73] Assignee: GAF Chemicals Corporation, Wayne, N.J.

[21] Appl. No.: 470,487

[22] Filed: Jan. 26, 1990

[51] Int. Cl.$^5$ .................. C08F 2/46; C08G 85/00; C08J 3/28
[52] U.S. Cl. .................. 522/31; 522/103; 522/170; 522/174; 522/181
[58] Field of Search .......... 522/31, 181, 170, 103, 522/174

[56] References Cited

U.S. PATENT DOCUMENTS

| | | | |
|---|---|---|---|
| 3,804,795 | 4/1974 | Perry et al. | 523/400 |
| 3,842,019 | 10/1974 | Kropp | 522/181 |
| 4,156,035 | 5/1979 | Tsao | 427/44 |
| 4,654,379 | 3/1987 | Lapin | 522/17 |

OTHER PUBLICATIONS

Higashimura et al., Effect of Polymerization Conditions on the Reactivity of Alkenyl Ethers Relative to Vinyl Ethers, Chemical Abstracts, vol. 79(2), 5702w, 1973.
J. A. Dougherty and F. J. Vara, L. R. Anderson, "Radcure '86": Conference Proceedings, Association for Finishing Processes, Baltimore, 1986, 15-1.
J. A. Dougherty and F. J. Vara, "Radcure Europe '87": Conference Proceedings, Association for Finishing Processes, Munich, West Germany, 1987, 5-1.
J. V. Crivello, J. L. Lee, D. A. Conlon, "Radiation Curing VI: Conference Proceedings", Association for Finishing Processes, Chicago, 1982, 4-28.
S. C. Lapin, "Radcure '86: Conference Proceedings", Association for Finishing Processes, Baltimore, 1986, 15—15.
S. C. Lapin, "RadTech '88-North America: Conference Proceedings", RadTech International, New Orleans, 1988, p. 395.
A. D. Ketley and Jung-Hsien Tsao, *J. Radiation Curing*, Apr. 1979, p. 22.
W. C. Perkins, *J. Radiation Curing*, Jan. 1981, p. 16.
P. C. Nelson and E. J. Moran, "RadTech '88-North America: Conference Proceedings", RadTech International, New Orleans, 1988, p. 120.
B. L. Brann, "RadTech Europe '89: Conference Proceedings", Radtech Europe, Florence, 1989, p. 565.
F. J. Vara and Jim Dougherty, Radcure '89 Conference Proceedings, "Concurrent Cationic/Free Radical Polymerization of Vinyl Ethers with Acrylate Functional Oligomers".
F. J. Vara and J. A. Dougherty, Water-Borne and Higher-Solids Coating Symposium, Feb. 1990, "Vinyl Ether in UV and EB Induced Cationic Curing".

*Primary Examiner*—Marion E. McCamish
*Assistant Examiner*—Mark A. Chapman
*Attorney, Agent, or Firm*—Marilyn J. Maue; Joshua J. Ward

[57] ABSTRACT

This invention relates to a radiation curable crosslinkable composition containing (a) from about 0.1 to about 5 wt. % of an initiator containing at least 25% cationic initiator, (b) from about 0 to about 60 wt. % of a polymerizable vinyl ether, epoxide, vinyloxy alkyl urethane or acrylate and (c) from about 35 to about 99.9% wt. % of a polyfunctional alkenyl ether having the formula

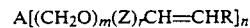

$$A[(CH_2O)_m(Z)_rCH=CHR]_n$$

wherein A is a carbon atom, —OCH=CHR or [$C_1$ to $C_{10}$ alkyl]$_{4-n}$; R is $C_1$ to $C_6$ alkyl; Z is $C_2$ to $C_8$ alkyleneoxy; r has a value of from 0 to 6; m has a value of from 0 to 1 and at least one of r and m has a positive value; n has a value of from 1 to 4, with the proviso that m is 0 and n is one when A is —OCH=CHR, n has a value of 2 or 3 when A is [$C_1$ to $C_{10}$ alkyl]$_{4-n}$ and n has a value of 4 when A is carbon. The invention also relates to the process of curing said composition and to a cured film on a substrate coated with the above composition.

13 Claims, No Drawings

RADIATION CURABLE CROSS LINKABLE COMPOSITIONS CONTAINING AN ALIPHATIC POLYFUNCTIONAL ALKENYL ETHER

BACKGROUND OF THE INVENTION

Certain radiation curable coatings and films such as those formed from the acrylates, particularly trimethylol propane triacrylate, trimethacrylate, pentaerythritol triacrylate, and hexanediol diacylate or methacrylate, are in great demand because of their rapid curing properties. However, these compounds are normally highly viscous liquids or solids and thus are unsuitable as diluents for other polymeric components of a radiation curable formulation. Indeed, such compounds themselves require the incorporation of a diluent or solvent for uniform substrate coating, control of coating thickness and curing at low temperatures. Accordingly, low viscosity monofunctional diluents are usually included in their formulations. While these diluents are reactive, they materially reduce the cross-linked density of the finished product and consequently lower abrasion resistance and ability to withstand chemical attack.

Although solvents have been used to reduce viscosity, they are detrimental in radiation curing due to their volatility which presents problems for uniform composition control unless their evaporation prior to radiant exposure is effected. Obviously, such procedure extends processing time and may pose environmental drawbacks.

To some extent, the drawbacks of high viscosity monomers can be reduced by curing at elevated temperatures. However, this alternative significantly adds to the cost of the overall operation in the expenditure of energy, temperature control and loss of more volatile components in the composition or blistering of the coating resulting from entrained volatiles.

Since acrylate monomers are not conducive to cationically induced radiation curing, they require free radical systems which are oxygen inhibited unless effected in an inert atmosphere, generally under a blanket of nitrogen. Although formulation with a photoinitiator which undergoes bimolecular reaction with a hydrogen donor minimizes the inhibitory effect of air, this benefit is realized at the expense of a greatly reduced cure rate. Also, it is found that polymerization or curing in free radical systems ceases almost immediately upon removal from the source of radiation; thus, the cured product often contains significant amounts of unpolymerized components. Accordingly, it is an aim of research to develop a monomer having the beneficial properties of acrylates but which is amenable to radiation curing at a rapid rate by cationically induced polymerization which is not oxygen inhibited and which permits continued polymerization after removal from the source of radiation exposure.

The inherent deficiencies of the acrylate systems can be partially overcome by the use of epoxy resins. Epoxy resins can be polymerized by normal radiation techniques using cationic photoinitiators such as iodonium, sulfonium and ferrocene salts of hexafluorophosphate, hexafluoroantimonate or hexafluoroarsonate to produce a tack free film. Although in such formulations tack free products are almost immediately obtained, polymerization of the mixture is incomplete. It is well known that the polymerization of epoxy resins is extremely slow and requires as much as several days to achieve their ultimate physical properties. Thus, thermal post curing is often employed to increase the rate of or to complete the polymerization.

Certain allyl compounds also have been used as coatings; however these monomers and their oligomers are not readily curable by cationic radiation. Thermal curing is generally required to increase the rate of polymerization. While allyl ethers such as polyethylene glycols are curable by UV light, they require a free radical initiated reaction which proceeds at a slow rate, generally over a period of from 2 to 10 hours in order to reach completion.

Finally, it is noted that the unsubstituted acrylates are sensitizers and skin irritants as well as being carcinogenic, so that specialized safety precautions must be taken to protect operators from exposure. Although alkoxylation has lessened irritancy of the acrylates, their carcinogenic properties are not reduced.

Accordingly it is an object of the present invention to overcome the above described deficiencies by an economical and commercially feasible composition and curing process.

Another object of this invention is to utilize a multifunctional cross-linking agent which is a liquid and which is more economically employed in an efficient ether cross-linking process.

Another object is to provide a non-toxic cross linkable homopolymeric compound suitable as a film or a substrate coating which possesses good adhesion, abrasion resistance and resistance to chemical attack.

Still another object is to provide a more economical process for cross-linking monomeric or polymeric vinyl or epoxy ethers which can be effected in the presence of air.

Another object is to provide a monomer which is curable at a rapid rate by cationically induced radiation.

These and other objects will become apparent from the following description and disclosure.

THE INVENTION

In accordance with this invention there is provided a radiation curable, cross linkable composition containing (a) from about 0.1 to about 5 wt. % of an initiator containing at least 25% of a cationic initiator, (b) from about 0 to about 60 wt. % of one or more polymerizable components of the group of a vinyl ether, epoxide, acrylate or a vinyloxy alkyl urethane and (c) from about 35 to about 99.9% wt. % of an aliphatic polyfunctional alkenyl ether having the formula

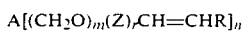

$$A[(CH_2O)_m(Z)_rCH=CHR]_n$$

wherein A is a carbon atom, $-OCH=CHR$ or $[C_1$ to $C_{10}$ alkyl$]_{4-n}$; R is $C_1$ to $C_6$ alkyl; Z is $C_2$ to $C_8$ alkyleneoxy; r has a value of from 0 to 6; m has a value of from 0 to 1 and at least one of r and m has a positive value; n has a value of from 1 to 4, with the proviso that m is 0 and n is one when A is $-OCH=CHR$, n has a value of 2 or 3 when A is $[C_1$ to $C_{10}$ alkyl$]_{4-n}$ and n has a value of 4 when A is carbon.

Of the above polyfunctional alkenyl ether compounds, those wherein R is methyl; A is $-OCH=CH$ (lower alkyl),-[lower alkyl]$_{4-n}$ or carbon are preferred. Also, when alkenyl ether is asymmetrical, the compound most preferably contains at least 35% of the cis isomer with respect to the trans isomer.

The most preferred compositions are those containing between about 20% and about 50% of component (b) and between about 50% and about 80% of component (c) where R is methyl.

The present polyfunctional alkenyl, preferably propenyl, ether compounds are homopolymerizable resins independently useful as protective coatings and are also effective cross-linking agents for polymerizable vinyl ethers having at least 6 carbon atoms or epoxides such as the divinyl ethers of the bis(hydroxyethyl) ether of bisphenol A, the divinyl ether of triethylene glycol, the divinyl ether of dimethylolcyclohexane, vinyloxyalkyl urethanes, e.g. divinyloxybutyl urethane oligomers, the diglycidyl ether of bisphenol A and its oligomers, bisphenol A epoxy acrylate and its oligomers, 3,4-epoxycyclohexyl methyl-3',4'-epoxycyclohexane carboxylate, the ethers disclosed in U.S. Pat. Nos. 4,388,450; 4,749,807; 4,775,732 and 4,751,271 and corresponding alkoxylated compounds and similar comonomers in monomeric or oligomeric form having a number average molecular weight up to about 5,000 or mixtures of said comonomers and/or copolymers. Such monomeric or polymeric vinyl ethers, epoxides, acrylates or urethanes can be reacted with the polyfunctional alkenyl ethers of this invention to form a cross-linked copolymeric product having a high cross-linked density and extremely high resistance to abrasion and chemical attack.

As stated above, the present polyfunctional alkenyl ethers, particularly the prop-1-enyl ethers, are homopolymerizable forming an exceedingly branched structure. As such, these agents can be used as rigid coatings on substrates which require an exceptionally high strength, resistance to abrasion and solvent attack. Substrates on which the copolymerized or homopolymerized agent is suitably coated include metal, wood, ceramic, plastic, leather, paper, glass and the like. The present composition is coated on the substrate by any convenient and conventional technique in the desired thickness, usually in a thickness of between about 0.1 to about 5 mils.

Instant alkenyl ethers having the structure $C[CH_2O(Z)_rCH=CHR]_4$ produce homopolymers and copolymers which are totally etheric in composition and which have greatly increased surface substantivity and other advantages derived from their poly etheric nature, such as high UV resistance and the ability to form hydrogels on exposure to water.

As cross-linking agents, the alkenyl ethers of this invention can be admixed with the above acrylate, urethane, epoxide or vinyl ether monomers or their oligomeric counterparts to effect cross-linking in the presence of a cationic initiator, such as a triphenyl sulfonium salt of phosphorous hexafluoride, diphenyl iodonium salt, a mixture of aromatic complex salts of butyrolactone (FX-512, supplied by Minnesota Mining & Mfg. Co.), a phenyl onium salt or an aryl alkyl onium salt, etc. The initiators suitable to effect polymerization reactions of the present invention include the above named cationic initiators which can be employed alone or in admixture with a free radical initiator to provide a hybrid system. Suitable free radical initiators include 1-hydrocyclohexyl phenyl ketone (e.g. IRGACURE 184), 2-hydroxy-2-methyl-1-phenyl-1-propan-1-one (DAROCUR 1173), 2,2-dichloro-1-(4-phenoxyphenyl) ethanone (SANDORAY 1000) and the like. Other free radical and cationic initiators which are suitably employed in this invention are those described by M.J.M. Abadie, Advantages and Development of Photochemical Initiators, in the European Coatings Journal 5/1988, pages 350-358. When initiator mixtures are employed, the free radical component can comprise up to 75%, preferably between about 30 and about 70%, of the cationic initiator component. A particularly preferred initiator mixture includes between about 30 wt. % and about 40 wt. % of FX-512 and between about 60 and about 70% of IRGACURE 184. The present initiator mixtures are recommended for blends of (b) and (c) where component (b) contains an acrylate. The total amount of initiator employed is generally between about 0.1 and about 5 wt. % with respect to reactant or reactants.

In accordance with this invention, one or more of the present aliphatic alkenyl ethers can be employed or blended with one or more of the polymerizable epoxides, vinyl ethers, acrylates or vinyloxy alkyl urethanes, thus benefiting from the properties of each monomer in the blend. Further, it is found that blends of the present propenyl ether and the divinyl ether of dimethylol cyclohexane enhance solubilization of the cationic initiator. Such blends may contain up to about 60%, preferably from about 20 to about 50% of component (b).

The propenyl ether of component (c) in the present composition, serves not only as a reactant, but also as an essential diluent for the vinyl ether and/or epoxide which compounds are highly viscous and difficult to apply as coatings. Thus. the propenyl ether provides a coatable composition without the need for extraneous diluents which in many cases can cause blisters and non-uniformity in the coating product.

The compositions of the present invention are cured within a period of up to one second by exposure to a source of radiation, e.g. UV light, electron beam, laser emissions, gamma rays etc. Radiation curing in the present cationic system takes place at a fast rate, e.g. from about 200 to about 1,000 feet per minute of coated surface or free formed film, depending upon the intensity and type of radiation employed. UV light radiation dosages at room temperature of from about 100 to about 1500 milli $J/cm^2$ are effective and dosages of from about 200 to about 600 milli $J/cm^2$ are preferred. Equivalent dosages for curing are employed when using alternative sources of radiation. For example, curing with electron beam radiation can be carried out at between about 0.5 and about 20 Mrads, preferably between about 1 and about 10 Mrads. Specific techniques for radiation curing are well known, thus further amplification is not required.

Since the present propenyl ethers are normally liquid, they can be directly mixed with the polymerizable vinyl ether, epoxide or vinyloxy alkyl urethane monomer or oligomer without further conditioning; however, in certain cases where dilution is desired, as in cases where higher molecular weight alkenyl ethers of this invention are employed as component (c) or where the blend provides a highly viscous mixture, the alkenyl ether can be dissolved in an inert organic solvent such as methyl ethyl ketone, toluene, a hydrocarbon, acetone, an ether or a halogenated compound such as methylene chloride. However, dilution with the above solvents should not exceed 50% when highly resistant coatings are required.

Alternatively, the alkenyl ether monomer or oligomer, in the absence of a comonomer can be applied directly to any of the above substrates and subjected to radiation for curing under the above conditions to form a more highly cross-linked homopolymeric protective coating.

It should also be understood that the present compositions can optionally contain minor amounts of conventional adjuvants such as a surfactant e.g. a fluorocarbon surfactant such as a mixture of fluoroaliphatic polymeric esters (FC-430 supplied by Minnesota Mining & Mfg. Co.) or a silicane copolymer surfactant (DC-193 supplied by Dow Corning Corp.) or others. It is also to be understood that the present compositions can be cured thermally or by radiation induced free radical polymerization; however, an advantage of this invention is the ability to cure the compositions by cationically induced radiation which avoids the disadvantages discussed in the foregoing disclosure. It is to be understood however that concurrent free radical and cationic induced polymerization using a mixture of such photoinitiators achieves benefits of this invention and is recommended where component (b) of the composition is an acrylate, e.g. bisphenol A epoxyacrylate.

A. Into an amber bottle, 50 grams of substantially pure (>95%) cis, cis dipropenyl ether of triethylene glycol, 50 grams of a diglycidyl ether of bisphenol A, 2 grams of the triphenyl sulfonium salt of hexafluorophosphate and 1 gram fluorocarbon surfactant were charged and thoroughly mixed. The resulting liquid mixture was coated on an aluminum panel with a #3 coating rod.

B. The above procedure was repeated except that a mixture of 48% cis, cis, 42% cis, trans mixture and 10% trans, trans was substituted for the cis, cis reactant in A.

C. The procedure in part A was repeated except that 3,4-epoxycyclohexylmethyl-3',4'-epoxycyclohexane carboxylate was substituted for the dipropenyl ether.

Each of the samples A, B, and C were coated in a thickness of 0.11-0.15 mil on an aluminum panel and then cured by exposure to UV light as described in Example 1. The cured coatings were evaluated and the results are reported in the following Table.

TABLE

|  | NO BAKE* A | BAKE** A | NO BAKE B | BAKE B | NO BAKE C | BAKE C |
| --- | --- | --- | --- | --- | --- | --- |
| Pencil Hardness (ASTM D3363) | F | 2H | F | 2H | H | 2H |
| % Adhesion (ASTM D3359) | — | 100 | — | 100 | — | 100 |
| % Adhesion 30 Min. Boiling H₂O | — | 100 | — | 100 | — | 100 |
| Double MEK Rubs | 1 | 2 | 1 | 2 | 1 | 2 |
| Reverse Impact (M-lbs) | — | 65 | — | 60 | 40 | 40 |
| Mandrel Bonds (inch - ASTM D3111) | ⅛ | ⅛ | ⅛ | ⅛ | ¼ | ¼ |
| Coating Thickness | — | 0.11 | — | 0.20 | — | 0.15 |
| Min Exposure for Tack-free coatings (m J/cm²) | 80 | — | 80 | — | 400 | — |

*Immediately after exposure to 400 m J/cm² UV.
**Baked for 10 minutes at 170° C. after UV exposure.

Having generally described the invention, reference is now had to the accompanying examples which illustrate preferred embodiments but which are not to be construed as limiting to the scope of the invention as more broadly set forth above and in the appended claims.

EXAMPLE 1

Into an amber bottle, 50 wt. % of diprop-1-enyl ether of diethylene glycol (70% cis, cis) and 50 wt. % of a diglycidyl ether of bisphenol A were charged and mixed at 50° C. for 1 hour. To this mixture, 2 parts/hundred parts of the triphenyl sulfonium salt of hexafluorophosphate were added with agitation. The resulting low viscosity liquid was directly coated on an aluminum panel in a thickness of 0.15 mil. The coated substrate was then exposed for less than one second at room temperature to 400 milli J/cm² radiation from a medium pressure mercury vapor lamp; after which the substrate having a highly crosslinked strongly adhesive coating* was removed. The coating is resistant to attack by methyl ethyl ketone and is abrasion resistant.

EXAMPLE 2

A two mil thick layer of a mixture of 98 wt. % of the tetraprop-1-enyl ether of pentaerythritol and 2.0 wt. % of the triphenyl sulfonium salt of hexafluorophosphate is applied to a polyester substrate. The coated layer is then crosslinked by exposure for about one second at room temperature to electron beam radiation at a dosage of 3 Mrad. The resulting highly crosslinked polymer exhibits strong adhesion, is highly resistant to chemical attack and has superior abrasion resistant properties.

EXAMPLE 3

It will be appreciated from the above results that changing the distribution from cis isomer to a cis/trans isomeric mixture did not materially affect the properties of the final coating. Example 3 also demonstrates the high cure speed of the di-propenyl ethers as compared to the di-epoxy compound.

EXAMPLE 4

A. Into an amber bottle, 50 grams of substantially pure (>95%) cis,cis- dipropenyl ether of triethylene glycol, 50 grams of a bisphenol A epoxy acrylate oligomer, 1 gram silicone surfactant (DC-193), 1 gram cationic photoinitiator (FX 512) and 1.5 gm free radical initiator (IRGACURE 184) were charged and mixed at 50° C. until homogeneous. The resulting liquid was coated on polyester using a #6 coating rod (approx. 0.5 mil) and cured by an exposure for less than 1 second at room temperature to 400 millijoules/cm² from a UV lamp.

B. The above procedure A was repeated except that the free radical initiator was omitted from the formulation.

C. The procedure in part A was repeated except that the cationic initiator was omitted from the formulation.

The cured coatings were evaluated immediately after UV exposure and the results are reported in the following Table.

TABLE

| Formula | A | B | C |
| --- | --- | --- | --- |
| Result | tack free | tack free | wet |
| Adhesion | 100% | 100% | none |
| Double MEK Rubs | >100 | 89 | none |
| Pencil Hardness | F | F | none |

This example illustrates the necessity of the cationic photoinitiator and the superior solvent resistance obtained using a cationic and free radical initiator.

EXAMPLE 5

A. Example 4A is repeated except that the 50 grams of cis,cis- dipropenyl ether of triethylene glycol is replaced with 50 grams of a 1 to 1 wt. % blend of cis,cis-dipropenyl ether of triethylene glycol and the divinyl ether of 1,4-cyclohexane dimethanol.

B. Example 4A is repeated except that the 50 grams of cis,cis-dipropenyl ether of triethylene glycol is replaced with 50 grams of the divinyl ether of 1,4-cyclohexane dimethanol. The cationic initiator failed to dissolve in the absence of the propenyl ether and an incompatible mixture was formed.

The above cured coatings were compared with that of 4A and were evaluated immediately after UV exposure. The results are as reported in the following table.

TABLE

| Formula | 4 A | 5 A | 5 B |
|---|---|---|---|
| Adhesion | 100% | 100% | incompatible |
| Double MEK Rubs | >100 | >100 | none |
| Pencil Hardness | F | 2H | none |

This example illustrates that coating hardness can be significantly improved by adding the divinyl ether of 1,4-cyclohexane dimethanol; and that, the dipropenyl ether of triethylene glycol is needed to insure compatibility.

EXAMPLE 6

Into an amber bottle, 50 grams of >95% cis, cis-dipropenyl ether of triethylene glycol, 50 grams of a divinyl ether of urethane oligomer (prepared as described in the Degree Thesis of Lennart Carlson, Dept. of Polymer Technology, the Royal Institute of Technology, Stockholm, Sweden, 1987), 4 phr* cationic photoinitiator (FX 512), and 1 phr fluorochemical surfactant (DC-193) were charged and mixed at 50° C. until homogeneous. The resulting liquid was coated on an aluminum panel to a 0.25 mil thickness using a #3 coating bar and then cured as described in Example 4. A tack free coating with the following properties was produced

| Pencil Hardness | 3B |
|---|---|
| Mandrel Bend | 3/16 inch |
| Double MEK rubs | 5 |

What is claimed is:

1. A radiation curable, cross linkable composition comprising (a) from about 0.1 to about 5 wt. % of an initiator containing at least 25% cationic initiator, (b) from about 0 to about 60 wt. % of a polymerizable vinyl ether, epoxy ether, epoxy aorylate and/or vinyloxy alkyl urethane and (c) from about 35 to about 99.9% wt. % of an aliphatic polyfunctional alkenyl ether having the formula $$A[(CH_2O)_m(Z)_rCH=CHR]_n$$

wherein A is a carbon atom, $-OCH=CHR$ or $[C_1$ to $C_{10}alkyl]_{4-n}$; R is $C_1$ to $C_6$ alkyl; Z is $C_2$ to $C_8$ alkyleneoxy; r has a value of from 0 to 6; m has a value of from 0 to 1 and n has a value of from 1 to 4, with the proviso that m is 0 and n is one when A is $-OCH=CHR$, n has a value of 2 or 3 when A is $[C_1$ to $C_{10}alkyl]_{4-n}$ and n has a value of 4 when A is carbon.

2. The composition of claim 1 consisting essentially of the aliphatic polyfunctional propenyl ether and a cationic initiator.

3. The composition of claim 1 wherein said composition contains between about 20 and about 50% of component (b) and between about 50 and about 80% of said alkenyl ether as a polyfunctional propenyl ether.

4. The composition of claim 1 wherein the aliphatic alkenyl ether is $$[lower alkyl]_4\ldots[CH_2O(Z)_rCH=CH(lower alkyl)]_n$$

where n has a value of 3.

5. The composition of claim 4 wherein said aliphatic alkenyl ether is the tetraprop-1-enyl ether of pentaerythritol.

6. The composition of claim 1 wherein the aliphatic alkenyl ether is $$(lower alkyl)CH_2O(Z)_rCH=CH(lower alkyl).$$

7. The composition of claim 6 wherein the aliphatic alkenyl ether is the dipropenyl ether of triethylene glycol.

8. The composition of claim 1 wherein the aliphatic alkenyl ether is asymmetrical and is a mixture containing at least about 35% cis isomer with respect to the trans isomer.

9. The composition of claim 1 wherein component (a) is a mixture of cationic and free radical initiators.

10. The composition of claim 9 wherein said composition contains between about 20 and about 50% of component (b).

11. The composition of claim 10 wherein component (b) is bisphenol A epoxy acrylate oligomer.

12. The composition of claim 10 wherein component (b) is the divinyl ether of 1,4-cyclohexane dimethanol.

13. The composition of claim 10 wherein component (b) is the divinyloxy butyl urethane oligomer.

* * * * *